United States Patent
Guerret

(10) Patent No.: US 9,809,514 B2
(45) Date of Patent: Nov. 7, 2017

(54) METHOD FOR PRODUCING (BROMOMETHYL)CYCLOPROPANE AND (BROMOMETHYL)CYCLOBUTANE

(71) Applicant: MELCHIOR MATERIAL AND LIFE SCIENCE FRANCE, Lacq (FR)

(72) Inventor: Olivier Guerret, Pern (FR)

(73) Assignee: MELCHIOR MATERIAL AND LIFE SCIENCE FRANCE, Lacq (FR)

(*) Notice: Subject to any disclaimer, the term of this patent is extended or adjusted under 35 U.S.C. 154(b) by 0 days.

(21) Appl. No.: 15/109,925

(22) PCT Filed: Dec. 1, 2014

(86) PCT No.: PCT/EP2014/076131
§ 371 (c)(1),
(2) Date: Jul. 6, 2016

(87) PCT Pub. No.: WO2015/101452
PCT Pub. Date: Jul. 9, 2015

(65) Prior Publication Data
US 2016/0355452 A1 Dec. 8, 2016

(30) Foreign Application Priority Data
Jan. 6, 2014 (FR) .................................... 14 50060

(51) Int. Cl.
*C07C 17/16* (2006.01)
*C07C 22/00* (2006.01)

(52) U.S. Cl.
CPC .......... *C07C 17/16* (2013.01); *C07C 2101/02* (2013.01); *C07C 2101/04* (2013.01)

(58) Field of Classification Search
CPC ..... C07C 17/16; C07C 22/00; C07C 2101/02; C07C 2101/04
See application file for complete search history.

(56) References Cited

U.S. PATENT DOCUMENTS

| 6,008,420 A | 12/1999 | Komoschinski et al. |
| 6,063,971 A | 5/2000 | Komoschinski et al. |
| 6,118,032 A | 9/2000 | Bayston et al. |
| 6,191,300 B1 | 2/2001 | Hyatt |

FOREIGN PATENT DOCUMENTS

| CN | 103435439 A | 12/2013 |
| EP | 0858988 A1 | 8/1998 |

OTHER PUBLICATIONS

CN 103435439 A Dec. 11, 2013, machine translations.*
Castro, "Replacement of Alcoholic Hydroxyl Groups by Halogens and Other Nucleophiles Via Oxyphosphonium Intermediates," Organic Reactions, vol. 29, Chapter 1, 1983, pp. 1-47, 157-162 (53 pages total).
French Preliminary Search Report for French Application No. 1450060, dated Sep. 11, 2014.
Furukawa et al., "Preparation of Alkyl Bromides from the corresponding Alcohols and $Me_2SBr_2$," Journal of the Chemical Society, Chemical Communications, Issue 6, Jan. 1, 1973, p. 212.
Hrubiec et al., "Regioselective Route to Sterically Hindered Cyclopropylcarbinyl Halides," Journal of Organic Chemistry, vol. 49, No. 3, Jan. 1984, pp. 431-435, XP000673291.
International Search Report (Forms PCT/ISA/220 and PCT/ISA/210) for International Application No. PCT/EP2014/076131, dated Feb. 13, 2015.
Roberts et al., "Small-Ring Compounds. IV. Interconversion Reactions of Cyclobutyl, Cyclopropylcarbinyl and Allylcarbinyl Derivatives," Journal of the American Chemical Society, vol. 73, Jun. 1951, pp. 2509-2520.

* cited by examiner

*Primary Examiner* — Jafar Parsa
(74) *Attorney, Agent, or Firm* — Birch, Stewart, Kolasch & Birch, LLP

(57) ABSTRACT

The present invention relates to a method for obtaining high purity (bromomethyl)cyclopropane and (bromomethyl)cyclobutane, starting respectively with cyclopropylmethanol and cyclobutylmethanol, under synthesis conditions that enable high productivity and high yield.

16 Claims, No Drawings

METHOD FOR PRODUCING (BROMOMETHYL)CYCLOPROPANE AND (BROMOMETHYL)CYCLOBUTANE

The present invention relates to a method of obtaining highly pure (bromomethyl)cyclopropane (2a) and (bromomethyl)cyclobutane (2b), starting respectively with cyclopropylmethanol (1a) and cyclobutylmethanol (1b) under synthesis conditions enabling high productivity on an industrial scale. These compounds are synthetic intermediates essential to many active substances.

Diagram 1: Structures of compounds 1a, b and 2a, b

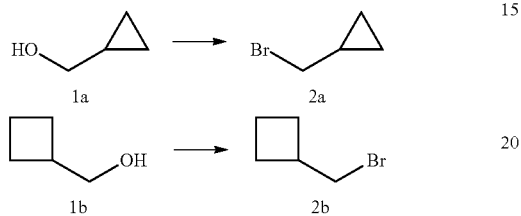

Because of the high reactivity of cyclopropyl and cyclobutyl strained rings, it is often preferable for the person skilled in the art to use these intermediates in the last steps of preparation of active substances. Consequently, the purity of the (bromomethyl)cyclobutane and (bromomethyl)cyclopropane molecules is essential since it directly influences the impurity profile of the active substances.

The prior art provides many examples of methods for synthesizing (bromomethyl)cyclobutane and (bromomethyl)cyclopropane molecules.

The first methods described did not make it possible to produce products with sufficient purities. In 1951, a bromination method using tribromophosphine was published (J. Am. Chem. Soc., 73, 1951, p. 2509-2520). Another method consists in using dimethylbromosulfonium bromide (J. Chem Soc., Chem. Commun., 1973, p. 212a). These methods are characterized by the use of a common bromination agent but these publications disclose that the purity obtained is poor due to the presence as by-products of bromoalkene difficult to separate from (bromomethyl)cyclopropanes or (bromomethyl)cyclobutanes because of the proximity of the boiling points, as explained in U.S. 61/913,001.

Another method is characterized by the use of a dimethylsulfonate intermediate (U.S. Pat. No. 6,191,300) or a tosyl intermediate (EP 0858988) which undergoes nucleophilic attack by sodium bromide, for example. This method is penalized by the significant weight of the electrophilic groups which result in heavy organic effluents.

In CN 103435439, a method for obtaining (bromomethyl)cyclobutane is disclosed. This method consists in mixing cyclobutyl carbinol, N-bromosuccinimide and triphenyl phosphite. However, this method has the disadvantage of requiring a temperature of about 40° C. and these conditions are not suited to the synthesis of (bromomethyl)cyclopropane. Furthermore, N-bromosuccinimide is a costly compound for industrial applications.

In J. Org. Chem., 49, 431 (1984), the authors used a method consisting in first preparing triphenylbromophosphonium bromide by reacting triphenylphosphine with bromine in dimethylformamide (DMF) and then reacting this compound with cyclopropylmethanol. U.S. Pat. No. 6,063, 971 reports next that the yields and purities claimed in the publication were not reproducible without suitably adjusting the reagent ratios. One limit of this method is the poor solubility of triphenylphosphine in DMF, which limits the productivity of this method.

To overcome this limitation, the Applicant found that they could advantageously replace the triarylphosphines of the previous method by triarylphosphites of general formula $P(OAr)_3$ because they make it possible, in selected solvents, to work with concentrations higher than those permitted by triarylphosphines. It is surprising that despite these higher concentrations in said solvents, the method of the present makes it possible to arrive at compounds 1a and 1b without causing degradation of the three- or four-membered rings which are very sensitive to nucleophilic or electrophilic conditions.

It is thus an object of the present to provide a method for preparing a compound (A) of the following formula:

(A)

in which R is a cyclobutane or cyclopropane group, comprising the following steps:
 a) solubilizing a triarylphosphite in a polar aprotic solvent,
 b) adding a bromine compound at a temperature of less than 15° C.,
 c) lowering the temperature to less than 0° C. after completion of the reaction of the bromine with the triarylphosphite,
 d) adding cyclobutylmethanol or cyclopropylmethanol at a temperature of less than 0° C.,
 e) recovering the compound (A).

In a preferred embodiment of the method according to the present invention, the triarylphosphite is a phosphite substituted by three aryl groups which can be selected from phenyl, tolyl, xylyl, for example.

In a particular embodiment, the polar aprotic solvent is selected from sulfoxides, substituted amides, sulfones and derivatives thereof, used alone or mixed. Preferably, the polar aprotic solvent is selected from dimethylformamide, sulfolane, dimethylsulfoxide, and mixtures thereof. More preferably, the polar aprotic solvent is dimethylformamide.

A polar aprotic solvent is a strongly solvating solvent. It is used when it is a question of reacting low polarity organic compounds with polar reagents or reagents which should generate anionic nucleophiles.

In a particular embodiment of the method according to the present invention, the mass ratio of triarylphosphite to polar aprotic solvent is between $1/10$ and $1/3$, particularly between $1/8$ and $1/4$.

Again preferably, the triarylphosphite is selected from the group consisting of triphenylphosphite, tris(4-alkylphenyl) phosphites such as tris(4-nonylphenyl)phosphite, tris(2,4-alkylphenyl)phosphites such as tris(2,4-di-terbutylphenyl) phosphite, tris(2,4-dihalophenyl)phosphites for which the halogen atoms are preferentially chlorine or bromine and tris(2,4-dinitrophenyl)phosphite. In a preferred embodiment, R is a cyclopropane group.

In another embodiment of the method according to the invention, step d) comprises adding cyclopropylmethanol, which makes it possible to obtain a compound (A) in which R is cyclopropane, the compound (A) thus being (bromomethyl)cyclopropane.

Therefore, the present invention has more particularly as an object to provide a method for preparing (bromomethyl) cyclopropane comprising the following steps:
  a) solubilizing a triarylphosphite in a polar aprotic solvent,
  b) adding a bromine compound at a temperature of less than 15° C.,
  c) lowering the temperature to less than 0° C. after completion of the reaction of the bromine with the triarylphosphite,
  d) adding cyclopropylmethanol at a temperature of less than 0° C.,
  e) recovering the (bromomethyl)cyclopropane.

In a particularly preferred embodiment of a method according to the invention, the triarylphosphite is triphenylphosphite.

It was difficult to foresee that the choice of triarylphosphite instead of triphenylphosphine would permit such productivity gains. The novelty of the method thus rests on the combination of the use of triarylphosphites in the presence of bromine in highly polar solvents such as dimethylformamide, sulfolane or dimethylsulfoxide. The fact that a phosphorus atom is substituted by three oxygen atoms greatly increases the polarity of the molecule, which makes it more soluble in strongly dissociating polar aprotic solvents such as DMF, DMSO or sulfolane. However, without better phosphite solubility in these solvents, due to the reactivity of the strained rings, it would not have been possible to concentrate the reaction medium. No work on bromination of compounds like 1a and 1b in the presence of triarylphosphite has been reported. Indeed, if one finds in the literature references to triphenylphosphite as to its use for bromination of alcohols (see for a review Castro, B. R. (1983). "Replacement of Alcoholic Hydroxy Groups by Halogens and Other Nucleophiles via Oxyphosphonium Intermediate". *Organic Reactions* 29: 1-162), the alcohols used for such reactions are not alcohols carrying 3- or 4-membered cyclic functions known for their ability to open easily in the presence of nucleophiles or electrophiles. Indeed, the mechanism of bromination (in the case of cyclopropane) in the presence of phosphite is as follows:

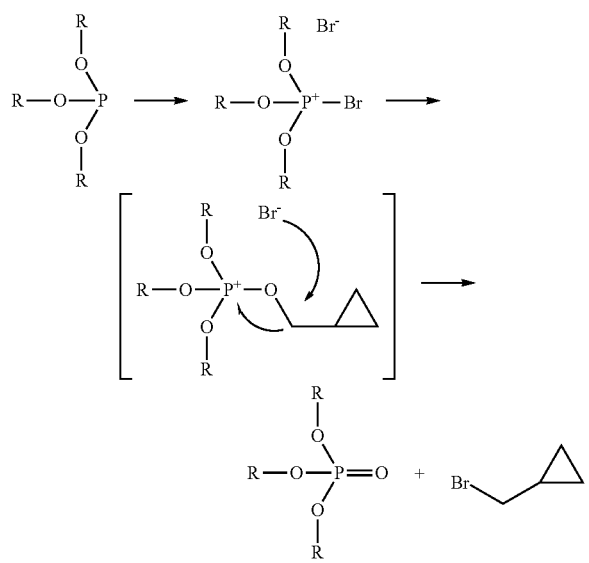

The secondary reaction, which is difficult to limit, is as follows:

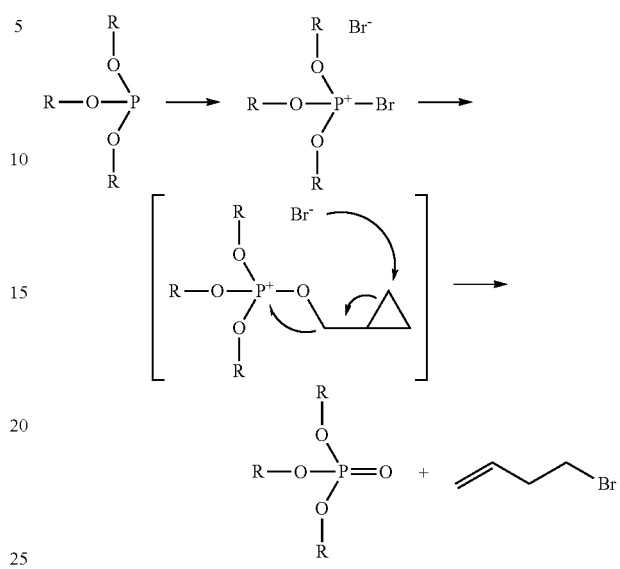

This exothermic reaction is promoted by the opening of the strained ring and a way to limit it consists in maintaining the temperature as low as possible. When the reaction is more concentrated, controlling heat exchange becomes essential to limiting an increase in temperature. When triphenylphosphine is used, too low a temperature causes precipitation and when the concentration is high the only remaining alternative is thus a greater dilution of the reaction medium. The use of triarylphosphite makes it possible to retain a homogeneous concentrated medium, which promotes completion of the reaction even at reduced temperature.

The amounts expressed in the present description as equivalents correspond to equivalents relative to the alcohol used, cyclopropylmethanol or cyclobutylmethanol. In a particular embodiment of the invention, the amount of triarylphosphite, particularly of triphenylphosphite, is between 0.9 and 2 equivalents, more particularly between 1 and 1.3 equivalents.

The polar aprotic solvent selected to solubilize the triarylphosphite is used in an amount between 4 and 8 volumes.

Typically, the solvent and the triarylphosphite are introduced into a temperature-controlled reactor equipped with a stirring system. The atmosphere within the reactor can be nitrogen.

The bromine compound added in step b) can be any compound containing bromine and able to generate diatomic bromine, $Br_2$, in the reaction medium. A bromine compound suitable for adding in step b) can be selected from the group consisting of diatomic bromine ($Br_2$), bromide salt solution in the presence of an oxidant such as hydrogen peroxide, or sodium tribromide solution, for example. Thus, preferably, the bromine compound added in step b) is diatomic bromine ($Br_2$). Preferably, the amount of bromine, particularly of $Br_2$, is between 0.9 and 2 equivalents of bromine, more particularly between 1 and 1.3 equivalents of bromine.

Addition of the bromine compound, particularly $Br_2$, is carried out at a temperature of less than 15° C., particularly at a temperature of less than 12° C., and the stirring speed is regulated according to the fluidity of the reaction medium. Once all the bromine is added, a very thick medium with a yellow solid suspension is obtained.

In a preferred embodiment of the method according to the present invention, the temperature of step b) is less than 12° C.

Once the reaction of the bromine with the triarylphosphite is complete, which can be evaluated by $^{31}$P NMR by following the disappearance of the phosphite signal and the appearance of bromophosphonium, the temperature is lowered to less than 0° C., more particularly to around −5° C. and below, still more particularly to around −10° C. and below, more preferably the temperature is between −15° C. and −10° C.

Therefore, an object of the present is to provide a method in which the temperature of step c) is lowered to less than 0° C., more particularly to −5° C. and below, still more particularly to −10° C. and below, more preferably to between −15° C. and −10° C.

This lowering of temperature makes it possible to control effectively the exothermicity of the reaction and to avoid by uncontrolled heating the formation of elimination or ring-opening by-products.

In order to obtain a compound according to the invention, cyclopropylmethanol or cyclobutylmethanol is then added to the reaction medium and the temperature of the reaction medium is regulated so as to be below 0° C., more particularly below −5°, more preferably between −10° C. and −5° C.

Therefore, an object of the present is to provide a method in which the temperature of step d) is less than 0° C., preferably below −5° C.

In a preferred embodiment, the method according to the present invention is such that the triarylphosphite is present in an amount corresponding to 0.9 to 2 equivalents, the solvent in an amount corresponding to 4 to 8 volumes of solvent, bromine in an amount corresponding to 1 to 1.3 equivalents of bromine and cyclopropylmethanol or cyclobutylmethanol in an amount corresponding to 1 equivalent.

The present invention also relates to a method according to the invention as described above which comprises an additional step of returning to room temperature and distillation in order to obtain the compound (A). Thus, after the addition of cyclobutylmethanol or cyclopropylmethanol, the temperature of the reaction medium is gradually returned to room temperature. The reaction medium containing the compound (A) is subjected to distillation according to means known to the person skilled in the art. For example, this distillation can be carried out by heating under reduced pressure. The distillation temperature can be between 50 and 70° C., more particularly around 65° C., and at a pressure between 1 mbar and 10 mbar, more particularly around 5 mbar.

After distillation, the fractions containing the product (A) can be washed and then dried.

Therefore, an object of the present is to provide a method in which the compound (A) obtained is subjected to washing and then to drying.

Washing of the compound (A) can be carried out by any adequate means known to the person skilled in the art, for example using buffer solution at pH 8 such as sodium or potassium carbonate solution.

Thus, the present invention aims at a method in which washing is carried out using calcium carbonate buffer solution at pH 8.

The compound (A) once washed can be dried using a desiccant in a manner known to the person skilled in the art. The desiccant can be selected from silica gels, calcium chloride, magnesium chloride, zeolites, lithium chloride or lithium bromide, for example.

Thus, the method according to the present invention comprises a drying step which is carried out using a desiccant selected from calcium chloride and magnesium chloride. In a particular embodiment, the radical R is a cyclobutane group and the compound (A) is (bromomethyl)cyclobutane and it is cyclobutylmethanol which is added in step d) of the method according to the present invention.

In another particular embodiment, the radical R is a cyclopropane group and the compound (A) is (bromomethyl)cyclopropane and it is cyclopropylmethanol which is added in step d) of the method according to the present invention.

Thus, in a particular embodiment, the present invention relates to a method as described above in which step d) consists in adding cyclobutylmethanol and the compound (A) is (bromomethyl)cyclobutane.

In another particular embodiment, the present invention relates to a method as described above in which step d) consists in adding cyclopropylmethanol and the compound (A) is (bromomethyl)cyclopropane.

This method has the advantage of providing a compound (A) with purity superior to 95%, particularly superior to 97%, more particularly superior to 98%. Such purity is particularly advantageous in terms of the use of a compound (A) according to the invention during the final steps of synthesis of pharmaceutical active agents for which high purity is required.

The yields obtained by virtue of the method according to the present invention are on the order of 70% and above, particularly 80% and above, which is singularly advantageous in an industrial context and particularly unexpected.

The method according to the present invention and the advantages thereof can be better understood with the aid of the following illustrative examples.

EXAMPLES

The raw materials are raw materials available from Sigma Aldrich.

The analytical method consists in gas chromatography (GC) analysis on an HP 5890 Series II apparatus. The chromatographic column is an Optima Delta-6 column (30 m, 0.25 mm, 0.25 μm).

The oven follows the following temperature profile: Initial temperature: 40° C.; Initial time: 5 min; Gradient: 5°/min; Final temperature: 125° C.; Duration 15 min.

The injector temperature is 250° C., that of the detector is 280° C., the volume injected is 1 μl and the pressure is 6 psi. The concentration of the sample is 75 g/l in tetrahydrofuran (THF).

The reactions are carried out in a 20 liter jacketed glass reactor and the distillations are carried out by means of a glass column having 10 theoretical plates.

Example 1

Method According to the Invention for Producing (Bromomethyl)Cyclopropane

Into a clean, dry reactor equipped with a stirrer and under nitrogen are successively loaded 4.63 kg of DMF (5.1 eqV) and then 4.53 kg of triphenylphosphite. 2.34 kg of bromine is then introduced while maintaining the temperature at less than 12° C. The stirring speed is regulated according to the fluidity of the reaction medium. When casting ends, a very thick medium with a yellow solid suspension is obtained.

The set point of the jacket is then adjusted to −12° C. and then 0.96 kg of cyclopropylmethanol is introduced in such a way as not to exceed a temperature of −5° C. On completion of the addition the whole is allowed to return slowly to room temperature. The set point of the jacket is then adjusted to 64° C. for distillation, which is carried out at a pressure of 13 mbar by collecting the first 24 to 30° C. fraction at the top of the column, then the second 30 to 40° C. fraction (partial reflux). Two fractions, F1 (1.38 kg) and F2 (293 g), are collected. The two fractions, after washing with carbonated water and then drying by means of $CaCl_2$, lead to a final product 2a (mass 1.316 kg) having a GC relative purity of 98.7% with a yield of 73%.

Example 2

Method According to the Invention for Producing (Bromomethyl)Cyclobutane

Into a clean, dry reactor equipped with a stirrer and under nitrogen are successively loaded 5.4 kg of DMF (5.1 eqV) and then 4.53 kg of triphenylphosphite. 2.34 kg of bromine is then introduced while maintaining the temperature at less than 12° C. The stirring speed is regulated according to the fluidity of the reaction medium.

The set point of the jacket is then adjusted to −12° C. and then 1.120 kg of cyclobutylmethanol is introduced in such a way as not to exceed a temperature of −5° C. At the end of the addition the whole is allowed to return slowly to room temperature. After distillation and washing, the final product 2b (mass 1.529 kg) having a GC relative purity of 98.3% is obtained with a yield of 78%.

Example 3

Comparative Example Implementing Triphenylphosphine with Cyclopropylmethanol

Into a clean, dry reactor equipped with a stirrer and under nitrogen are successively loaded 4.63 kg of DMF (5.1 eqV) and then 3.84 kg of triphenylphosphite; the temperature is maintained at 40° C. with stirring for 60 minutes in order to promote solubilization of the triphenylphosphine. Partial reprecipitation is observed during cooling before the addition of $Br_2$. 2.34 kg of bromine is then introduced while maintaining the temperature at less than 12° C. At the conclusion of the addition of bromine, the medium is very pasty and hard to stir. The set point of the jacket is then adjusted to −12° C. and then 0.96 kg of cyclopropylmethanol is introduced in such a way as not to exceed a temperature of −5° C. Slight fluidification is observed after addition of cyclopropylmethanol, but it is insufficient for the medium, which remains very pasty, to be able to be distilled. The final product is thus not recoverable. The difficulties encountered during this synthesis are related to the poor solubility of triphenylphosphine in DMF.

The invention claimed is:
1. A method for preparing a compound (A) of the following formula:

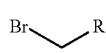

(A)

in which R is a cyclobutane or cyclopropane group, comprising the following steps:
 a) solubilizing a triarylphosphite in a polar aprotic solvent,
 b) adding a bromine compound at a temperature of less than 15° C.,
 c) lowering the temperature to less than 0° C. after completion of the reaction of the bromine with the triarylphosphite,
 d) adding cyclobutylmethanol or cyclopropylmethanol at a temperature of less than 0° C.,
 e) recovering the compound (A).

2. The method according to claim 1 wherein the polar aprotic solvent is selected from sulfoxides, substituted amides, sulfones and derivatives thereof, used alone or mixed.

3. The method according to claim 1 wherein the polar aprotic solvent is selected from dimethylformamide, sulfolane, dimethylsulfoxide, and mixtures thereof.

4. The method according to claim 1, wherein the triarylphosphite is selected from the group consisting of triphenylphosphite, tris(4-alkylphenyl)phosphites, tris(2,4-alkylphenyl)phosphites, tris(2,4-dihalophenyl)phosphites for which the halogen atoms are chlorine or bromine and tris(2,4-dinitrophenyl)phosphite.

5. The method according to claim 1, wherein the triarylphosphite is triphenylphosphite.

6. The method according to claim 1 wherein the mass ratio of triarylphosphite to polar aprotic solvent is between 1/10 and 1/3.

7. The method according to claim 1 wherein the bromine compound is Br2.

8. The method according to claim 1, comprising an additional step of returning to room temperature and distillation of the compound (A).

9. The method according to claim 8 wherein the compound (A) obtained is subjected to washing and then to drying.

10. The method according to claim 9 wherein washing is carried out using sodium carbonate buffer solution at pH 8.

11. The method according to claim 9 wherein drying is carried out using a desiccant selected from calcium chloride and magnesium chloride.

12. The method according to claim 1 wherein step d) consists in adding cyclobutylmethanol and the compound (A) is (bromomethyl)cyclobutane.

13. The method according to claim 1 wherein step d) consists in adding cyclopropylmethanol and the compound (A) is (bromomethyl)cyclopropane.

14. The method according to claim 4, wherein the tris(4-alkylphenyl)phosphites is tris(4-nonylphenyl)phosphite.

15. The method according to claim 4, wherein the tris(2,4-alkylphenyl)phosphites is tris(2,4-di-terbutylphenyl)phosphite.

16. The method according to claim 6 wherein the mass ratio of triarylphosphite to polar aprotic solvent is between 1/8 and 1/4.

* * * * *